(12) United States Patent
Katz et al.

(10) Patent No.: US 11,911,167 B2
(45) Date of Patent: Feb. 27, 2024

(54) AUTOMATIC MESH RESHAPING OF AN ANATOMICAL MAP TO EXPOSE INTERNAL POINTS OF INTEREST

(71) Applicant: BIOSENSE WEBSTER (ISRAEL) LTD., Yokneam (IL)

(72) Inventors: Natan Sharon Katz, Atlit (IL); Benjamin Cohen, Haifa (IL); Aharon Turgeman, Zichron Ya'acov (IL); Lior Zar, Poria Illit (IL); Fady Massarwa, Baka Al Gharbiyya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 563 days.

(21) Appl. No.: 17/151,825

(22) Filed: Jan. 19, 2021

(65) Prior Publication Data
US 2022/0225924 A1    Jul. 21, 2022

(51) Int. Cl.
*A61B 5/367*      (2021.01)
*A61B 5/333*      (2021.01)
(Continued)

(52) U.S. Cl.
CPC .............. *A61B 5/367* (2021.01); *A61B 5/333* (2021.01); *A61B 5/339* (2021.01); *A61B 34/10* (2016.02); *G06T 15/08* (2013.01); *G06T 19/00* (2013.01); *G16H 20/40* (2018.01); *G16H 50/50* (2018.01); *A61B 5/287* (2021.01); *A61B 5/6859* (2013.01); *A61B 5/7435* (2013.01); *A61B 2018/00375* (2013.01); *A61B 2018/00577* (2013.01); *A61B 2034/105* (2016.02); *A61B 2034/107* (2016.02);
(Continued)

(58) Field of Classification Search
CPC ......... A61B 5/367; A61B 5/339; A61B 5/333; A61B 5/287; A61B 5/6859; A61B 2018/00375; A61B 2018/00577; G16H 20/40; G16H 50/50; G06T 15/08; G06T 19/00; G06T 2210/41; G06T 2219/004; A16B 2034/107
See application file for complete search history.

(56) References Cited

U.S. PATENT DOCUMENTS 6,226,542 B1 *   5/2001   Reisfeld .................. G06T 17/20
                                                              600/407
6,301,496 B1 * 10/2001   Reisfeld .................. A61B 5/287
                                                              600/407
(Continued)

FOREIGN PATENT DOCUMENTS

EP          4046574 A1     8/2022

OTHER PUBLICATIONS

PCT Search report for corresponding International Appln. No. PCT/IB2022/061824 dated Mar. 13, 2023.

*Primary Examiner* — Catherine M Voorhees
*Assistant Examiner* — Roland Dinga

(57) ABSTRACT

A method includes receiving or generating a volume map of at least a portion of a cavity of an organ of a body including a plurality of mapped locations, and a point cloud of locations in the cavity marked for treatment. The volume map is updated by removing a portion of the mapped locations, so that the locations marked for treatment fall on a surface of the volume map. Using the updated volume map, a map of at least a portion of the cavity is generated, the map including the locations marked for treatment. The map is displayed to user.

18 Claims, 4 Drawing Sheets

(51) Int. Cl.
*A61B 5/339* (2021.01)
*A61B 34/10* (2016.01)
*G06T 15/08* (2011.01)
*G06T 19/00* (2011.01)
*G16H 20/40* (2018.01)
*G16H 50/50* (2018.01)
A61B 5/00 (2006.01)
A61B 5/287 (2021.01)
A61B 18/00 (2006.01)

(52) U.S. Cl.
CPC .... *G06T 2210/41* (2013.01); *G06T 2219/004* (2013.01)

(56) References Cited

U.S. PATENT DOCUMENTS

| | | |
|---|---|---|
| 11,113,899 B1 | 9/2021 | Massarwa |
| 2006/0286501 A1 | 12/2006 | Chishti |
| 2006/0290695 A1 | 12/2006 | Salomie |
| 2009/0264742 A1 | 10/2009 | Markowitz |
| 2011/0160569 A1* | 6/2011 | Cohen .................... G06T 19/00 600/424 |
| 2017/0325891 A1 | 11/2017 | Harlev |
| 2019/0231287 A1* | 8/2019 | Krimsky ................. G06T 7/149 |
| 2020/0197095 A1* | 6/2020 | Harlev ................... G06T 17/00 |

* cited by examiner

AUTOMATIC MESH RESHAPING OF AN ANATOMICAL MAP TO EXPOSE INTERNAL POINTS OF INTEREST

FIELD OF THE INVENTION

The present invention relates generally to electroanatomical (EA) mapping, and particularly to automatic editing of cardiac EA maps.

BACKGROUND OF THE INVENTION

Software-based editing tools for assisting in the interpretation of a mapped cavity of an organ were previously proposed in the patent literature. For example, in the field of dentistry, U.S. Patent Application Publication No. 2006/0286501 describes using a computer to create a plan for repositioning an orthodontic patient's teeth. The computer receives an initial digital data set representing the patient's teeth at their initial positions and a final digital data set representing the teeth at their final positions. The computer then uses the data sets to generate treatment paths along which the teeth will move from the initial positions to the final positions. In some embodiments, the individual tooth models include data representing hidden tooth surfaces, such as roots imaged through x-ray, CT scan, or MRI techniques. Tooth roots and hidden surfaces also can be extrapolated from the visible surfaces of the patient's teeth.

As another example, U.S. Patent Application Publication No. 2017/0325891 describes methods directed at generating a three-dimensional surface representation of an anatomic structure such as a heart cavity. More specifically, the three-dimensional surface representation of the anatomic structure is constrained relative to one or more anchor portions corresponding to received input regarding the location of anatomic features of the anatomic structure. The resulting three-dimensional surface representation includes salient features of the anatomic structure and, therefore, can be useful as visualization tools during any of various different medical procedures, including, for example, cardiac ablation.

SUMMARY OF THE INVENTION

An embodiment of the present invention that is described hereinafter provides a method including receiving or generating a volume map of at least a portion of a cavity of an organ of a body including a plurality of mapped locations, and a point cloud of locations in the cavity marked for treatment. The volume map is updated by removing a portion of the mapped locations, so that the locations marked for treatment fall on a surface of the volume map. Using the updated volume map, a map of at least a portion of the cavity is generated, the map including the locations marked for treatment. The map is displayed to a user.

In some embodiments, removing the portion of the mapped locations includes identifying one or more of the locations marked for treatment that fall in an interior of the volume map, and removing the portion so that the identified locations marked for treatment fall on the surface of the volume map.

In some embodiments, identifying a location marked for treatment that falls in the interior of the volume map includes determining that a vector, from the location marked for treatment to a respective projected location on the surface, is opposite to an outward-pointing normal to the surface at the projected location.

In an embodiment, the locations marked for treatment are locations on a cardiac wall tissue, and are marked for ablation.

In another embodiment, generating the map includes generating an electroanatomical (EA) map of at least a portion of the wall tissue.

In some embodiments, removing the portion of the mapped locations includes projecting the locations marked for treatment to respective locations on the surface of the volume map, and removing the portion of the volume map that includes a surface connecting the locations marked for treatment with the projected locations.

In some embodiments, removing the surface connecting the locations marked for treatment with the projected locations includes removing a surface defined as a surface between a first curve generated by interconnecting the locations marked for treatment, and a second curve generated by interconnecting the projected locations.

In other embodiments, removing the portion of the volume includes defining, between each location marked for treatment and a respective projected location on the surface, a respective distance embedded in the surface, and defining the removed portion based on the distance.

In an embodiment, defining the removed portion of volume map includes defining a sphere having a diameter corresponding to the distance.

In another embodiment, wherein displaying the map to the user includes presenting one or more icons at the locations marked for treatment.

There is additionally provided, in accordance with another embodiment of the present invention, a system including a memory and a processor. The memory is configured to store a plurality of mapped locations acquired in a cavity of an organ of a body, and a point cloud of locations in the cavity marked for treatment. The processor is configured to (i) receive or generate a volume map of at least a portion of the cavity including the plurality of mapped locations, (ii) update the volume map by removing a portion of the mapped locations, so that the locations marked for treatment fall on a surface of the volume map, (iii) using the updated volume map, generate a map of at least a portion of the cavity, including the locations marked for treatment, and (iv) display the map to a user.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
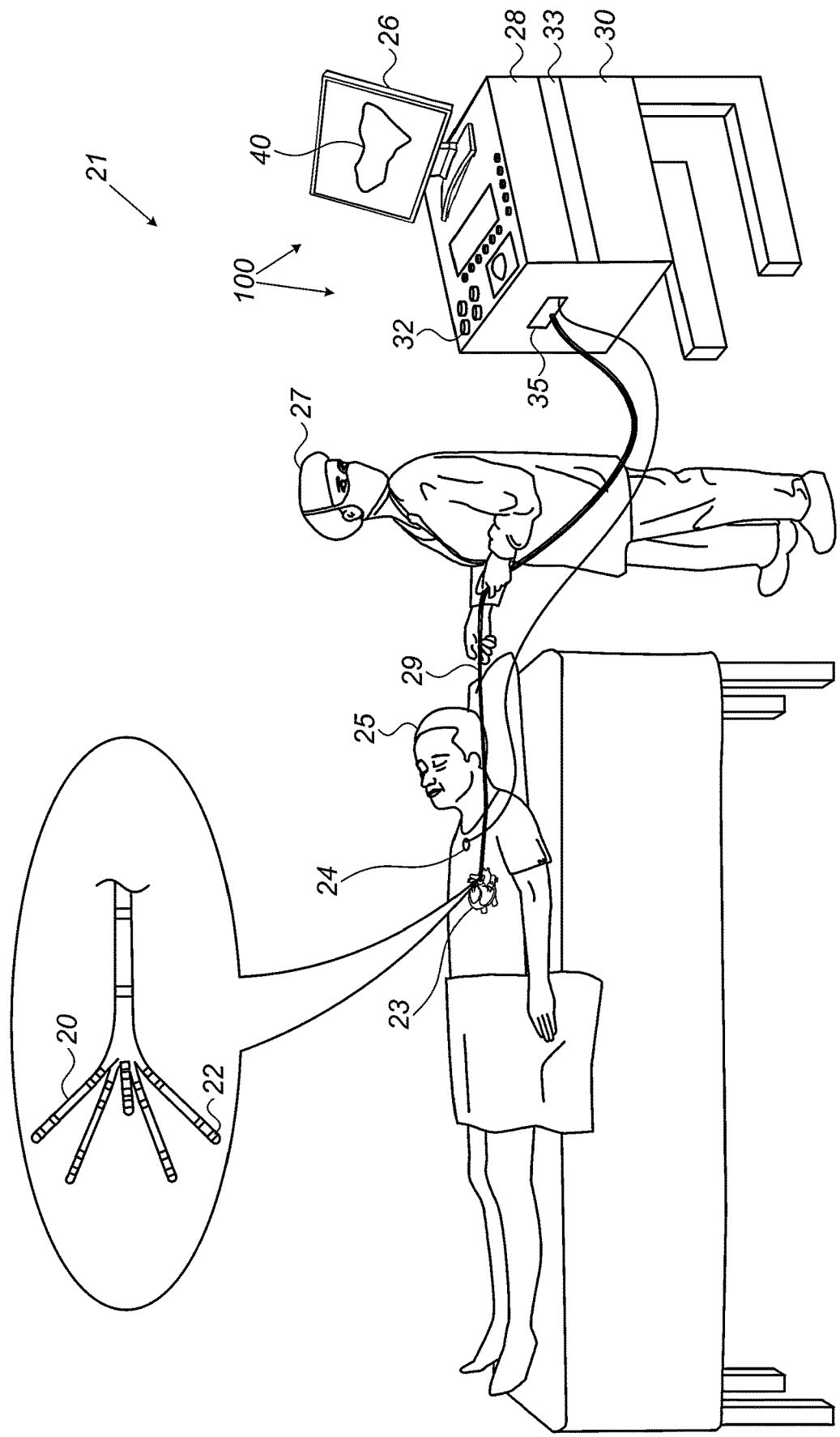
FIG. 1 is a schematic, pictorial illustration of a system for electroanatomical (EA) mapping, in accordance with an exemplary embodiment of the present invention.

A cavity of an organ of a patient, such as a cardiac cavity, also called hereinafter cardiac chamber, can be mapped (e.g., electroanatomically mapped) using a mapping catheter having one or more suitable sensors, such as electrodes, fitted at its distal end for mapping within the organ. Using location signals generated by the various sensors, a processor may calculate the sensor locations within the organ (e.g., the locations of sensing electrodes inside the cardiac cavity). Using the calculated locations, the processor may further derive an anatomical map of the cavity surface. In case of a cardiac cavity (e.g., cardiac chamber), the processor may derive an electroanatomical (EA) map of the cavity surface. In some embodiments, such an EA map also graphically indicates arrhythmogenic locations over the cavity wall tissue that should be ablated for treatment of arrhythmia.

Typically, therefore, before a cardiac ablation procedure, the cardiac chamber is mapped, to (i) obtain a volume representation of the cardiac chamber anatomy, and (ii) acquire a point cloud of locations in the cardiac chamber to be marked for ablation. At least some of the locations marked for ablation are typically located along a curve. For example, in a fast anatomical mapping (FAM) of a cardiac chamber, point locations for ablation on an inner surface of the cavity are drawn using acquired EA data. Subsequently, a physician may ablate the locations along the curve to block an aberrant electrophysiological signal, as in the case of isolating a pulmonary vein ostium in a left atrium.

However, erroneous catheter locations may also be acquired and automatically added to a FAM-constructed cavity surface during FAM reconstruction. Examples of such undesired data points include cavity wall locations distorted by being pushed outward by the catheter, as well as incorrect wall locations due to respiration-induced movement.

The accumulation of such undesired locations affects the accuracy of the reconstructed EA map. To address these inaccuracies, during or after acquisition, a physician, or a specialist helping the physician, may manually edit the surface that is generated from the acquired points to correct for the errors. This manual editing typically involves erasing locations and/or removing ("shaving") entire portions from the computed surface. However, this manual editing is a time-consuming process.

Moreover, in some cases erroneous catheter locations may obstruct or hide markings that point to wall tissue locations selected for treatment, such as cardiac wall tissue locations selected for ablation. Typically, while locations for ablation are marked (e.g., overlaid) on the map as icons (e.g., "visitags"), some of the icons may become invisible because they appear inside the chamber, rather than on its outer surface, due to the above, or other, mapping errors.

Embodiments of the present invention use an underlying assumption that the mapped locations marked for treatment (e.g., ablation) are correct, and that any obstruction of such marks by other locations on the cavity wall is due to erroneous mapping of the wall tissue. Such mapping errors cause locations marked for treatment to erroneously appear inside the chamber. This results in icons (e.g., visitag icons) pointing at these locations being hidden in a typical, non-transparent view of the map of the cavity of the organ.

To overcome such errors, a processor corrects the mapping of the cavity so that the locations marked for treatment fall on the cavity wall. In an embodiment, the processor receives or generates an EA map of at least a portion of a volume of a cardiac cavity, and a point cloud of locations marked for treatment (e.g., ablation). The processor identifies that one or more of the locations marked for treatment fall in an interior of the volume, and in response updates the volume by removing a portion of the mapped locations, so that the locations marked for treatment fall on a surface of the volume of the chamber map. Using the updated EA mapping data, the processor generates a map of at least a portion of the cavity, comprising the locations marked for treatment, and displays the map to user.

In another embodiment, to remove a portion of the mapped locations, the processor projects the locations marked for treatment onto a modeled surface of the cavity. The processor then joins the locations marked for treatment by a first spline, and joins the projected locations by a second spline. A "ball rolling" algorithm is then used: A "ball," having a variable radius found by connecting respective locations marked for treatment and projected locations, is "rolled" along the two splines, and anatomical locations in the chamber volume and surface are removed from the cloud. The chamber surface is then reconstructed using the updated data set to reveal the original locations marked for treatment (e.g., to make their icons visible in an external view of the model). In general, a shape other than ball can be used, such as of an ellipsoid having a variable width and diameter.

By exposing hidden landmarks (e.g., icons) of locations marked for treatment, the disclosed technique may assist the physician to improve the quality of complicated diagnostic tasks performed during diagnostic catheterizations, such as marking (e.g., by visitag icons) tissue locations mapped for ablation. Another advantage of the disclosed technique is reducing the editing time of portions of the EA map, e.g., when done manually for this purpose.

System Description

FIG. 1 is a schematic, pictorial illustration of a system 21 for electroanatomical (EA) mapping, in accordance with an embodiment of the present invention. FIG. 1 depicts a physician 27 using a Pentaray® EA mapping catheter 29 to perform an EA mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23.

A processor 28 in a console 30 receives these signals via an electrical interface 35, and uses information contained in these signals to construct an EA map 40 that processor 28 stores in a memory 33. During and/or following the procedure, processor 28 may display EA map 40 on a display 26. User controls 32 of a user interface 100 enable physician 27 to communicate with processor 28 and command editing and/or highlighting portions of EA map 40. Controls 32 may include, for example, a trackball and control knobs, as well as a keyboard. Other elements of user interface 100 may include touch screen functionality of display 26.

During the procedure, a tracking system is used to track the respective locations of sensing electrodes 22, such that each of the signals may be associated with the location at which the signal was acquired. For example, the Active Catheter Location (ACL) system, made by Biosense-Webster (Irvine California), which is described in U.S. Pat. No. 8,456,182, whose disclosure is incorporated herein by reference, may be used. In the ACL system, a processor estimates the respective locations of the electrodes based on impedances measured between each of the sensing electrodes 22, and a plurality of surface electrodes 24, that are coupled to the skin of patient 25. For example, three surface electrodes 24 may be coupled to the patient's chest, and another three surface electrodes may be coupled to the patient's back. (For ease of illustration, only one surface electrode is shown in FIG. 1.) Electric currents are passed between electrodes 22 inside heart 23 of the patient and surface electrodes 24. Processor 28 calculates an estimated location of all electrodes 22 within the patient's heart based on the ratios between the resulting current amplitudes measured at surface electrodes 24 (or between the impedances implied by these amplitudes) and the known locations of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as those based on measuring voltage signals. Other types of sensing catheters, such as the Lasso® Catheter (produced by Biosense Webster) or a basket catheter may equivalently be employed. Contact sensors may be fitted at the distal end of EA mapping catheter 29. As noted above, other types of electrodes, such as those used for ablation, may be utilized in a similar way and fitted to electrodes 22 for acquiring the needed location data. Thus, an ablation electrode used for collecting location data is regarded, in this case, as a sensing electrode. In an optional embodiment, processor 28 is further configured to indicate the quality of physical contact between each of the electrodes 22 and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 3, that enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Automatic Mesh Reshaping of an Anatomical Map for Internal Points of Interest

Figure 2:
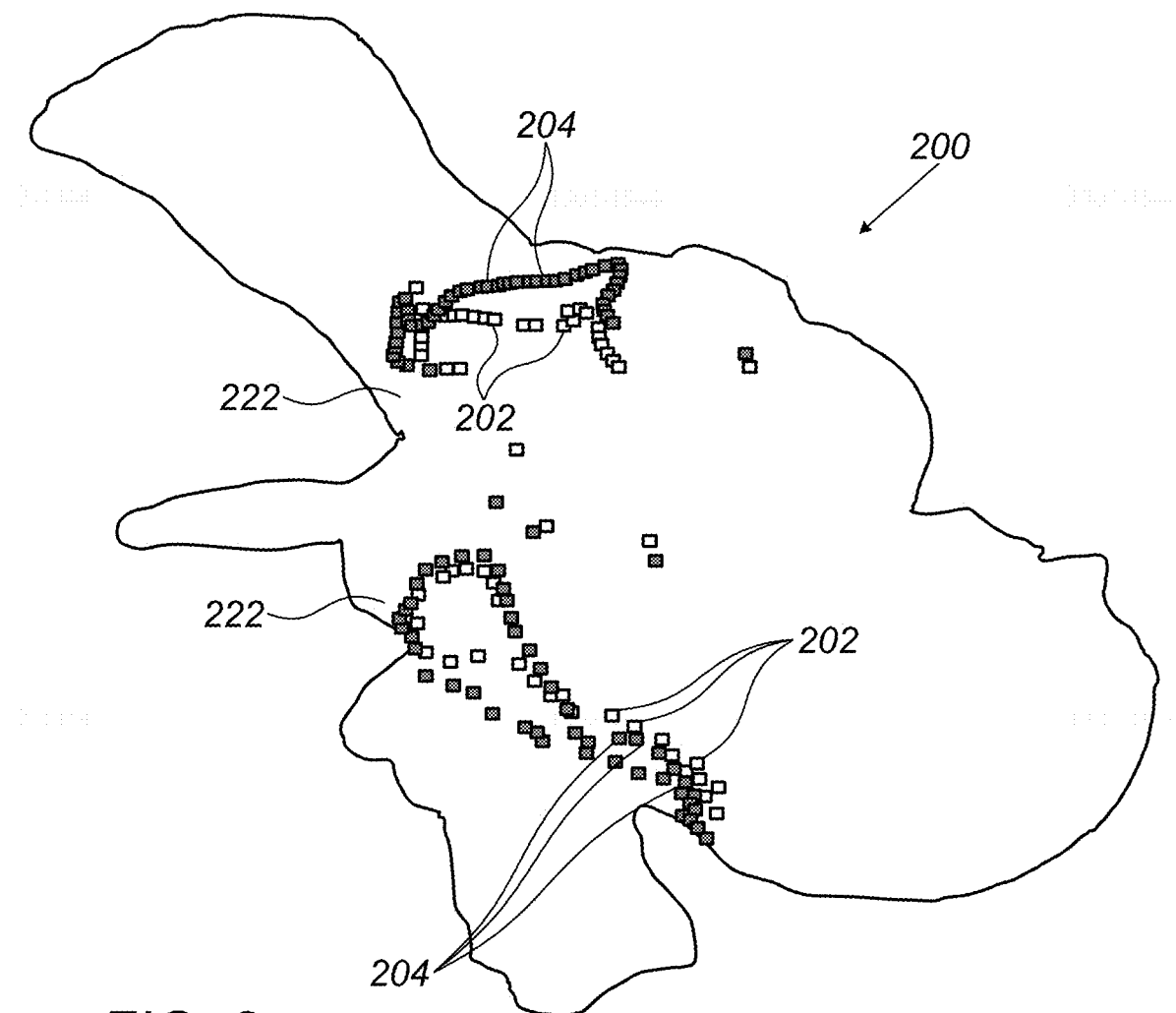
FIG. 2 is a volume-rendered semi-transparent EA map of a left atrium showing locations marked for ablation and respective projected locations on a surface of the EA map, in accordance with an exemplary embodiment of the present invention.

FIG. 2 is a volume-rendered semi-transparent EA map 200 of a left atrium showing locations marked for ablation (202) and respective projected locations 204 on a surface of the EA map, in accordance with an embodiment of the present invention.

FIG. 2 shows a map for clarity and simplicity of presentation only. The disclosed process does not necessarily require generating such an initial map. Rather, acquisition data comprising locations is received in a processor, and the processor applies the disclosed steps to the mapped volume.

As seen, mapped locations marked for ablation 202 are each along a circumference of an ostium 222 of a pulmonary vein. The mapped location may define a contour (not shown) along which a subsequent ablation is performed to isolate an arrhythmia.

As noted above, errors in map 200 may cause icons of locations 202 to be hidden in a non-transparent view.

In one embodiment of the disclosed technique, the processor identifies only locations 202 marked for treatment that fall in an interior of the mapped volume by determining if a vector between each location 202 marked for treatment and its respective projected surface location 204 is opposing an outward-pointing normal to the surface of the cavity at the projected location. Subsequently, the processor projects locations 202 to surface locations 204, in order to subsequently generate a map in which icons of locations 202 are visible, as described below.

In another embodiment, the processor projects all points marked for treatment, without attempting to identify which of the locations is internal. If a point is already on the surface, then the rolled ball diameter, or local volume to remove, will be zero or negligible.

While the shown cavity is of a left atrium, the description holds for cavities of other organs and for different treatments than ablation.

Figure 3:
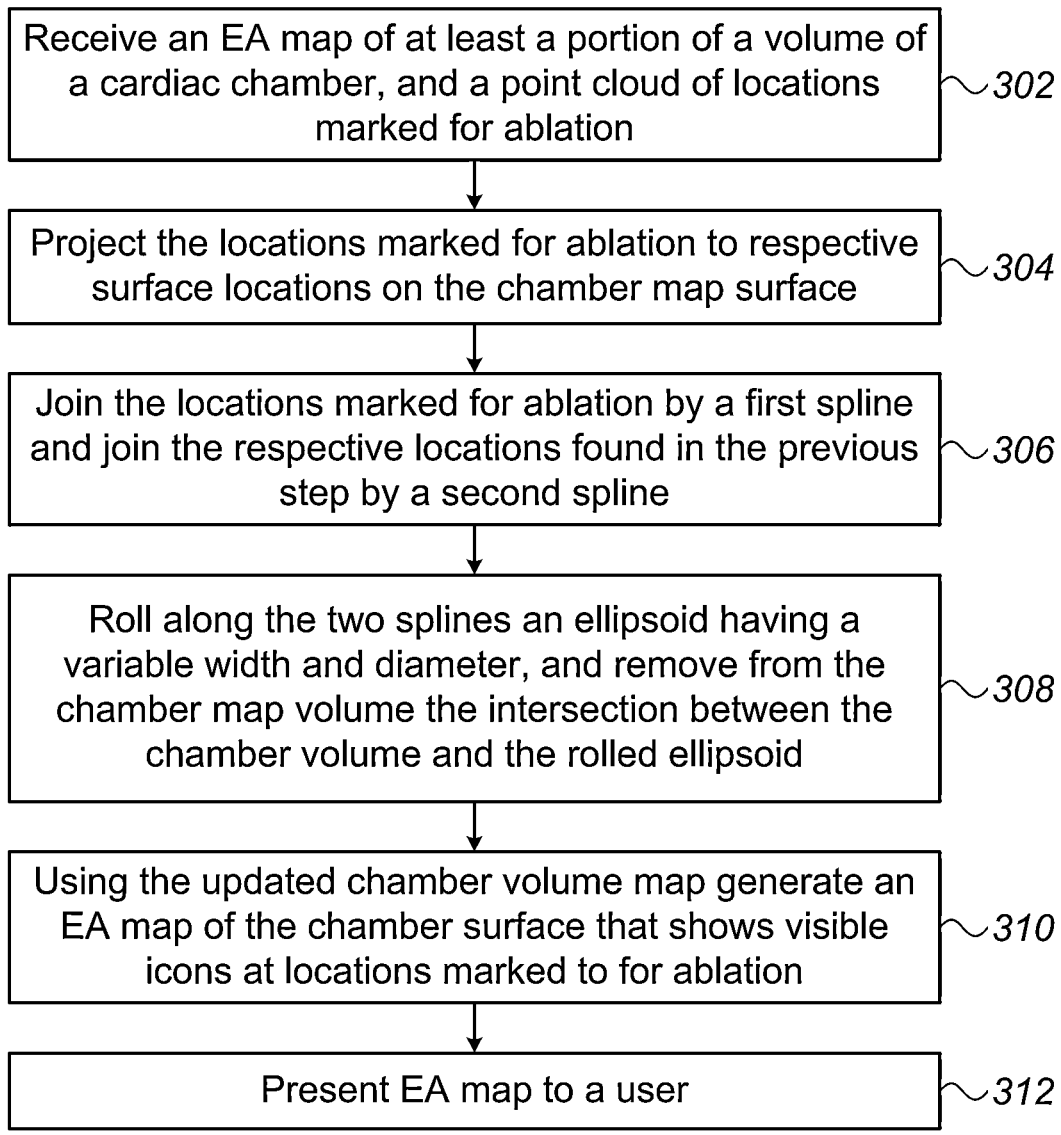
FIG. 3 is a flow chart that schematically illustrates a method for exposing locations of a cardiac cavity marked for ablation, in accordance with an exemplary embodiment of the present invention.

FIG. 3 is a flow chart that schematically illustrates a method for exposing locations of a cardiac cavity marked for ablation, in accordance with an embodiment of the present invention. The algorithm, according to the presented embodiment, carries out a process that begins with processor 28 receiving an EA map of at least a portion of a volume of a cardiac chamber, and a point cloud of locations marked for ablation, at a data receiving step 302. At this stage some of the location marked for ablation may comprise hidden icons.

Next, processor 28 projects the locations marked for ablation to respective locations on a surface of the chamber map volume, at a data projection step 304.

At a data connection step 306, processor 28 joins locations marked for ablation by a first spline, and joins the respective projected locations found in step 304 by a second spline.

Next, at a point cloud updating step 308, processor 28 generates an updated volume by automatically removing portions of the volume that comprise a surface connecting the locations marked for ablation with the projected locations. For example, the processor "rolls" a ball having a variable diameter (or "rolls" the aforementioned ellipsoid) along the two splines and removes from the chamber map volume the intersection between the chamber volume and the rolled ball, or ellipsoid.

At an EA map generation step 310, using the updated mapped data, or chamber volume map, processor 28 generates an EA map, such as map 440 shown below in FIG. 4B, of the portion of the cardiac cavity comprising visible icons that mark ablation locations.

Finally, at a map displaying step 312, processor 28 presents the EA map to a user.

The example flow chart shown in FIG. 3 is chosen purely for the sake of conceptual clarity. For example, in alternative embodiments, the cavity is of an organ other than a heart.

Reshaped Mesh of an Anatomical Map

Figure 4B:
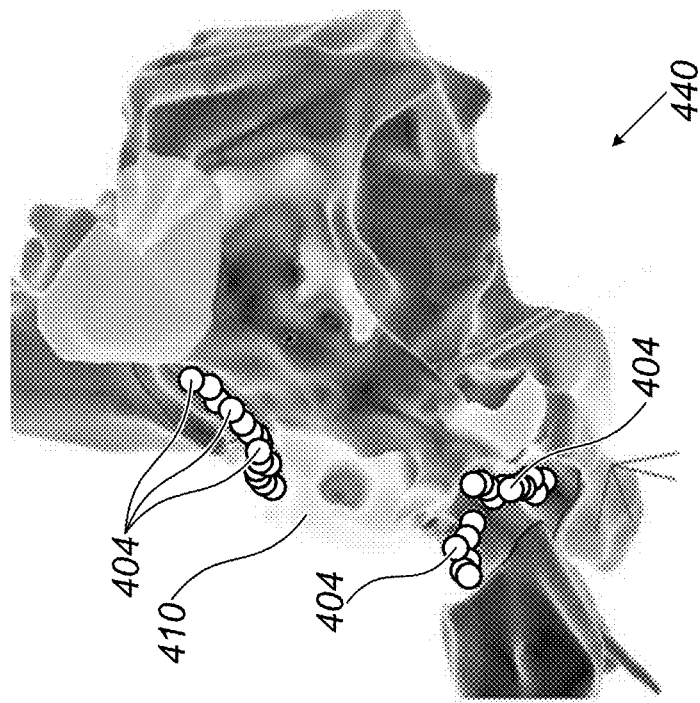
FIGS. 4A and 4B are volume-rendered non-transparent maps of a cardiac cavity showing respectively a surface that hides icons of locations for ablation, and the mesh reshaped surface with the icons exposed at locations marked for ablation, in accordance with exemplary embodiments of the present invention.
Figure 4A:
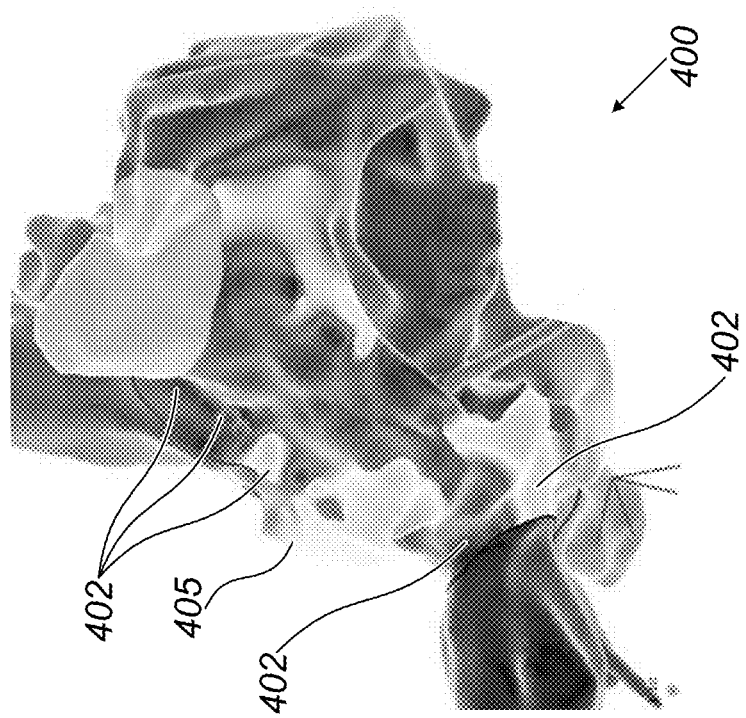

FIGS. 4A and 4B are volume-rendered non-transparent EA maps 400 and 440 of a cardiac cavity showing, respectively, a surface 405 that hides (402) icons of locations for ablation, and the mesh reshaped surface with the icons (404) exposed at locations marked for ablation, in accordance with embodiments of the present invention.

As seen in FIG. 4A, almost all the icons marking locations 402 for ablation on two ostia of a pulmonary vein of a left atrium are hidden under surface 405. In FIG. 4B, on the other hand, the regenerated surface 410 exposes respective locations, as shown by icons 404.

A physician may use map 440 to perform the required ablation.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for exposing hidden landmarks of locations for treatment in an anatomical map, comprising:
    receiving or generating a volume map of at least a portion of a cavity of an organ of a body comprising a plurality of mapped locations, and a point cloud of locations in the cavity marked for treatment;
    updating the volume map by removing a portion of the mapped locations, so that the locations marked for treatment fall on a surface of the volume map, wherein removing the portion of the mapped locations comprises projecting the locations marked for treatment to respective locations on the surface of the volume map, and removing the portion of the volume map that comprises a surface connecting the locations marked for treatment with the projected locations;
    using the updated volume map, generating a map of at least a portion of the cavity, comprising the locations marked for treatment; and
    displaying the map to a user.

2. The method according to claim 1, wherein removing the portion of the mapped locations comprises identifying one or more of the locations marked for treatment that fall in an interior of the volume map, and removing the portion so that the identified locations marked for treatment fall on the surface of the volume map.

3. The method according to claim 2, wherein identifying a location marked for treatment that falls in the interior of the volume map comprises determining that a vector, from the location marked for treatment to a respective projected location on the surface, is opposite to an outward-pointing normal to the surface at the projected location.

4. The method according to claim 1, wherein the locations marked for treatment are locations on a cardiac wall tissue, and are marked for ablation.

5. The method according to claim 4, wherein generating the map comprises generating an electroanatomical (EA) map of at least a portion of the wall tissue.

6. The method according to claim 1, wherein removing the surface connecting the locations marked for treatment with the projected locations comprises removing a surface defined as a surface between a first curve generated by interconnecting the locations marked for treatment, and a second curve generated by interconnecting the projected locations.

7. The method according to claim 1, wherein removing the portion of the volume map comprises defining, between each location marked for treatment and a respective projected location on the surface, a respective distance embedded in the surface, and defining the removed portion based on the distance.

8. The method according to claim 7, wherein defining the removed portion of volume comprises defining a sphere having a diameter corresponding to the distance.

9. The method according to claim 1, wherein displaying the map to the user comprises presenting one or more icons at the locations marked for treatment.

10. A system for exposing hidden landmarks of locations for treatment in an anatomical map, comprising:
    a memory, which is configured to store a plurality of mapped locations acquired in a cavity of an organ of a body, and a point cloud of locations in the cavity marked for treatment; and
    a processor, which is configured to:
        receive or generate a volume map of at least a portion of the cavity comprising the plurality of mapped locations;
        update the volume map by removing a portion of the mapped locations, so that the locations marked for treatment fall on a surface of the volume map;
        using the updated volume map, generate a map of at least a portion of the cavity, comprising the locations marked for treatment; and
        display the map to a user,
        wherein the processor is configured to project the locations marked for treatment to respective locations on the surface of the volume map, and to remove the portion of the volume map that comprises a surface connecting the locations marked for treatment with the projected locations.

11. The system according to claim 10, wherein the processor is configured to identify one or more of the locations marked for treatment that fall in an interior of the volume map, and to remove the portion so that the identified locations marked for treatment fall on the surface of the volume map.

12. The system according to claim 11, wherein the processor is configured to identify a location marked for treatment that falls in the interior of the volume map by determining that a vector, from the location marked for treatment to a respective projected location on the surface, is opposite to an outward-pointing normal to the surface at the projected location.

13. The system according to claim 10, wherein the locations marked for treatment are locations on a cardiac wall tissue, and are marked for ablation.

14. The system according to claim 13, wherein the processor is configured to generate the map by generating an electroanatomical (EA) map of at least a portion of the cardiac wall tissue.

15. The system according to claim 10, wherein the processor is configured to remove the surface connecting the locations marked for treatment with the projected locations by removing a surface defined as a surface between a first curve generated by interconnecting the locations marked for treatment, and a second curve generated by interconnecting the projected locations.

16. The system according to claim 10, wherein the processor is configured to remove the portion of the volume by defining, between each location marked for treatment and a respective projected location on the surface, a respective distance embedded in the surface, and defining the removed portion based on the distance.

17. The system according to claim 16, wherein the processor is configured to define the removed portion of volume map by defining a sphere having a diameter corresponding to the distance.

18. The system according to claim 10, wherein the processor is configured to display the map to the user by presenting one or more icons at the locations marked for treatment.

* * * * *